US012642696B2

(12) United States Patent
Heeren et al.

(10) Patent No.: US 12,642,696 B2
(45) Date of Patent: Jun. 2, 2026

(54) SYSTEM AND METHODS FOR A CASSETTE CAPTURE MECHANISM FOR PHACOEMULSIFICATION SURGICAL APPLICATIONS

(71) Applicant: Johnson & Johnson Surgical Vision, Inc., Santa Ana, CA (US)

(72) Inventors: Tammo Heeren, Aliso Viejo, CA (US); John C. Dunne, Jr., Costa Mesa, CA (US); Matthew Flowers, Aliso Viejo, CA (US)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 958 days.

(21) Appl. No.: 17/124,465

(22) Filed: Dec. 16, 2020

(65) Prior Publication Data

US 2021/0205507 A1    Jul. 8, 2021

Related U.S. Application Data

(60) Provisional application No. 62/949,432, filed on Dec. 17, 2019.

(51) Int. Cl.
A61M 1/00 (2006.01)
A61F 9/007 (2006.01)

(52) U.S. Cl.
CPC .... A61F 9/00745 (2013.01); A61B 2217/005 (2013.01); A61B 2217/007 (2013.01); A61M 2205/121 (2013.01); A61M 2205/122 (2013.01); A61M 2205/14 (2013.01)

(58) Field of Classification Search
CPC .......... A61F 9/00745; A61B 2217/005; A61B 2217/007; A61M 2205/121; A61M 2205/122; A61M 2205/14
See application file for complete search history.

(56) References Cited

U.S. PATENT DOCUMENTS

| | | | |
|---|---|---|---|
| 4,276,023 | A | 6/1981 | Phillips et al. |
| 4,479,760 | A | 10/1984 | Bilstad et al. |
| 4,537,561 | A | 8/1985 | Xanthopoulos |
| 4,713,051 | A | 12/1987 | Steppe et al. |
| 4,735,558 | A | 4/1988 | Kienholz et al. |
| 4,758,200 | A | 7/1988 | Von Moltke |
| 4,758,220 | A | 7/1988 | Sundblom et al. |
| 4,758,238 | A | 7/1988 | Sundblom et al. |
| 4,770,654 | A | 9/1988 | Rogers et al. |
| 4,790,816 | A | 12/1988 | Sundblom et al. |
| 4,798,580 | A | 1/1989 | DeMeo et al. |

(Continued)

FOREIGN PATENT DOCUMENTS

| | | | |
|---|---|---|---|
| EP | 424687 A1 | 5/1991 |
| EP | 1310267 A2 | 5/2003 |

(Continued)

*Primary Examiner* — Connor J Tremarche

(57) ABSTRACT

A system and method for detecting and/or capturing a cassette is disclosed. The cassette capture mechanism may be used with a surgical console of a surgical system, wherein the system has a cassette receiving area having at least two alignment sensors and a plurality of capture plungers; and at least two capture hooks which may engage with a cassette, wherein at least one of the at least two alignment sensors produces a signal indicative of the presence of a cassette.

19 Claims, 12 Drawing Sheets

(56) References Cited

U.S. PATENT DOCUMENTS

| | | | |
|---|---|---|---|
| 4,810,242 A | 3/1989 | Sundblom et al. | |
| 4,819,317 A | 4/1989 | Bauer et al. | |
| 4,925,444 A | 5/1990 | Orkin et al. | |
| 4,933,843 A | 6/1990 | Scheller et al. | |
| 4,941,518 A | 7/1990 | Williams et al. | |
| 4,963,131 A | 10/1990 | Wortrich | |
| 5,020,535 A | 6/1991 | Parker et al. | |
| 5,091,656 A | 2/1992 | Gahn | |
| 5,106,366 A | 4/1992 | Steppe | |
| 5,145,227 A * | 9/1992 | Monford, Jr. | B25J 19/005 |
| | | | 414/737 |
| 5,195,960 A | 3/1993 | Hossain et al. | |
| 5,242,404 A | 9/1993 | Conley et al. | |
| 5,273,517 A | 12/1993 | Barone et al. | |
| 5,282,787 A | 2/1994 | Wortrich | |
| 5,445,506 A | 8/1995 | Afflerbaugh et al. | |
| 5,460,490 A | 10/1995 | Carr et al. | |
| 5,464,391 A | 11/1995 | Devale | |
| 5,470,312 A | 11/1995 | Zanger et al. | |
| 5,499,969 A | 3/1996 | Beuchat et al. | |
| 5,531,697 A | 7/1996 | Olsen et al. | |
| 5,697,910 A | 12/1997 | Cole et al. | |
| 5,702,357 A | 12/1997 | Bainbridge et al. | |
| 5,871,492 A | 2/1999 | Sorensen | |
| 5,910,110 A | 6/1999 | Bastable | |
| 5,928,257 A | 7/1999 | Kablik et al. | |
| 5,938,655 A | 8/1999 | Bisch et al. | |
| 6,109,895 A | 8/2000 | Ray et al. | |
| 6,129,656 A | 10/2000 | Blakeslee et al. | |
| 6,511,454 B1 | 1/2003 | Nakao et al. | |
| 7,070,578 B2 | 7/2006 | Leukanech et al. | |
| 7,244,240 B2 | 7/2007 | Nazarifar et al. | |
| 7,465,285 B2 | 12/2008 | Hutchinson et al. | |
| 7,479,123 B2 | 1/2009 | Briggs | |
| 7,764,370 B2 | 7/2010 | Williams et al. | |
| 8,070,712 B2 * | 12/2011 | Muri | A61M 3/0201 |
| | | | 604/32 |
| 8,491,528 B2 | 7/2013 | Muri et al. | |
| 9,386,922 B2 | 7/2016 | Ross et al. | |
| 9,492,317 B2 | 11/2016 | Links et al. | |
| 9,579,429 B2 | 2/2017 | Williams et al. | |
| 9,713,660 B2 | 7/2017 | Baxter et al. | |
| 9,757,275 B2 | 9/2017 | Muri et al. | |
| 9,877,865 B2 | 1/2018 | Links | |
| 9,895,262 B2 | 2/2018 | Ross et al. | |
| 10,265,217 B2 | 4/2019 | Ross | |
| 10,441,461 B2 | 10/2019 | Muri et al. | |
| 10,583,040 B2 | 3/2020 | Ross et al. | |
| 2003/0106861 A1 | 6/2003 | Gibbs et al. | |
| 2004/0106915 A1 | 6/2004 | Thoe | |
| 2004/0124157 A1 | 7/2004 | Briggs et al. | |
| 2004/0127840 A1 | 7/2004 | Gara et al. | |
| 2004/0202561 A1 | 10/2004 | Hershberger et al. | |
| 2005/0069419 A1 | 3/2005 | Cull et al. | |
| 2005/0070859 A1 | 3/2005 | Cull et al. | |
| 2005/0070871 A1 | 3/2005 | Lawton et al. | |

| | | | |
|---|---|---|---|
| 2005/0095153 A1 | 5/2005 | Demers et al. | |
| 2005/0209552 A1 | 9/2005 | Beck et al. | |
| 2005/0228266 A1 | 10/2005 | McCombs | |
| 2007/0231205 A1 * | 10/2007 | Williams | F04B 43/12 |
| | | | 422/63 |
| 2007/0233003 A1 | 10/2007 | Radgowski et al. | |
| 2007/0253463 A1 | 11/2007 | Perry et al. | |
| 2007/0253850 A1 | 11/2007 | Williams | |
| 2008/0015493 A1 | 1/2008 | Childers et al. | |
| 2008/0015515 A1 | 1/2008 | Hopkins et al. | |
| 2008/0027368 A1 | 1/2008 | Kollar et al. | |
| 2009/0087327 A1 | 4/2009 | Voltenburg, Jr. et al. | |
| 2010/0140149 A1 | 6/2010 | Fulkerson et al. | |
| 2010/0249693 A1 | 9/2010 | Links | |
| 2011/0208047 A1 | 8/2011 | Fago | |
| 2011/0251569 A1 | 10/2011 | Turner et al. | |
| 2011/0295193 A1 | 12/2011 | Fitzgerald et al. | |
| 2012/0078181 A1 | 3/2012 | Smith et al. | |
| 2012/0083735 A1 | 4/2012 | Pfouts | |
| 2012/0083736 A1 | 4/2012 | Pfouts et al. | |
| 2013/0169412 A1 | 7/2013 | Roth | |
| 2013/0184676 A1 | 7/2013 | Kamen et al. | |
| 2013/0245543 A1 * | 9/2013 | Gerg | A61M 1/77 |
| | | | 604/30 |
| 2013/0336814 A1 | 12/2013 | Kamen et al. | |
| 2014/0088558 A1 | 3/2014 | Holtwick et al. | |
| 2014/0178215 A1 * | 6/2014 | Baxter | A61F 9/00745 |
| | | | 417/360 |
| 2014/0188076 A1 | 7/2014 | Kamen et al. | |
| 2014/0276424 A1 | 9/2014 | Davis et al. | |
| 2015/0088058 A1 * | 3/2015 | Harr | G16H 20/60 |
| | | | 604/67 |
| 2016/0295523 A1 * | 10/2016 | Hermann | H04W 52/283 |
| 2016/0296366 A1 * | 10/2016 | Ross | A47B 81/00 |
| 2018/0141748 A1 * | 5/2018 | Chenvainu | B65F 1/163 |
| 2018/0292906 A1 * | 10/2018 | Kato | H04N 5/74 |
| 2019/0188992 A1 * | 6/2019 | Bodurka | H04L 43/10 |
| 2019/0221100 A1 * | 7/2019 | Yu | A61B 5/6804 |
| 2019/0255231 A1 | 8/2019 | Köppel et al. | |
| 2019/0307607 A1 | 10/2019 | Ross | |

FOREIGN PATENT DOCUMENTS

| | | |
|---|---|---|
| EP | 1779879 A1 | 5/2007 |
| EP | 1839690 A1 | 10/2007 |
| EP | 1857128 A1 | 11/2007 |
| JP | S58167333 A | 10/1983 |
| JP | S62204463 A | 9/1987 |
| JP | 2005195653 A | 7/2005 |
| WO | 9315777 A2 | 8/1993 |
| WO | 9324082 A1 | 12/1993 |
| WO | 9405346 A1 | 3/1994 |
| WO | 9818507 A1 | 5/1998 |
| WO | 0228449 A2 | 4/2002 |
| WO | 05084728 A2 | 9/2005 |
| WO | 2007143677 A2 | 12/2007 |
| WO | 2007149637 A2 | 12/2007 |
| WO | 2013142009 A1 | 9/2013 |

* cited by examiner

SYSTEM AND METHODS FOR A CASSETTE CAPTURE MECHANISM FOR PHACOEMULSIFICATION SURGICAL APPLICATIONS

CROSS-REFERENCE TO RELATED APPLICATIONS

This application claims the benefit under 35 U.S.C. § 119 (e) of U.S. Provisional Patent Application No. 62/949,432, filed Dec. 17, 2019, which is incorporated herein by reference in its entirety.

BACKGROUND OF THE INVENTION

Field of Technology

The present invention relates generally to the sensing of a surgical cassette and, more specifically, to the sensing of the orientation and location of a cassette relative to a surgical console.

Description of the Background

The optical elements of the eye include both a cornea (at the front of the eye) and a lens within the eye. The lens and cornea work together to focus light onto the retina at the back of the eye. The lens also changes in shape, adjusting the focus of the eye to vary between viewing near objects and far objects. The lens is found just behind the pupil and within a capsular bag, the capsular bag being a thin, relatively delicate structure which separates the eye into anterior and posterior chambers.

With age, clouding of the lens or cataracts is fairly common. Cataracts may form in the hard central nucleus of the lens, in the softer peripheral cortical portion of the lens, or at the back of the lens near the capsular bag. Cataracts can be treated by the replacement of the cloudy lens with an artificial lens. Phacoemulsification systems often use ultrasound energy to fragment the lens and aspirate the lens material from within the capsular bag. This may allow the capsular bag to be used for positioning of the artificial lens, and maintains the separation between the anterior portion of the eye and the vitreous humor in the posterior chamber of the eye.

During cataract surgery and other therapies of the eye, accurate control over the volume of fluid within the eye is highly beneficial. For example, while ultrasound energy breaks up the lens and allows it to be drawn into a treatment probe with an aspiration flow, a corresponding irrigation flow may be introduced into the eye so that the total volume of fluid in the eye does not change excessively. If the total volume of fluid in the eye is allowed to get too low at any time during the procedure, the eye may collapse and cause significant tissue damage. Similarly, excessive pressure within the eye may strain and injure tissues of the eye.

While a variety of specific fluid transport mechanisms may be used in phacoemulsification and other treatment systems for the eyes, aspiration flow systems can generally be classified in two categories: 1) volumetric-based aspiration flow systems using positive displacement pumps (e.g. peristaltic); and 2) vacuum-based aspiration systems using a vacuum source, typically applied to the aspiration flow through an air-liquid interface within a reservoir (e.g. Venturi). Both systems may be incorporated into one treatment system and/or cassette. Cassette ("pack") systems can be used to couple peristaltic pump drive rotors and/or vacuum systems of the surgical consoles to an eye treatment handpiece, with the flow network conduit of the cassette being disposable to avoid cross-contamination between different patients.

In traditional ophthalmic surgery, fluid from the fluid source is also used to irrigate the eye during a procedure. As mentioned above, the irrigation fluid serves to maintain proper intraocular pressure and to replace fluid during aspiration of emulsified lens fragments. The irrigation source is typically a 500 ml bottle or drip bag of saline solution. One issue is that, during ophthalmic surgery, the potential exists for the saline solution to be depleted, turning the irrigation dry. Though an unlikely scenario, the potential consequences are substantial-severe corneal burns, capsular tear requiring vitrectomy or additional vitro-retinal surgery, damage to the structure of the eye, and/or loss of vision.

To mitigate such occurrences, staff operating a system typically begins each procedure with a fresh irrigation source prior to each case, and monitor the fluid visually throughout surgery. In some instances, flow sensors are used to measure flow out of the irrigation source. However, conventional configurations do not efficiently provide relative irrigation source volumes and only provide warnings when a detected flow indicates a very low irrigation source volume. As such, improvements are needed in the art to address these issues.

SUMMARY

A system and method for detecting and/or capturing a cassette is disclosed, comprising a cassette capture mechanism that may be used with a surgical console of a surgical system. The system may comprise a cassette receiving area having at least two alignment sensors and a plurality of capture plungers; and at least two capture hooks which may engage with a cassette, wherein at least one of the at least two alignment sensors produces a signal indicative of the presence of a cassette.

DESCRIPTION OF THE DRAWINGS

The accompanying drawings are included to provide a further understanding of the invention, and are incorporated in and constitute a part of this specification. The drawings illustrate disclosed embodiments and/or aspects and, together with the description, serve to explain the principles of the invention, the scope of which is determined by the claims.

DETAILED DESCRIPTION OF THE INVENTION

Figure 1A:
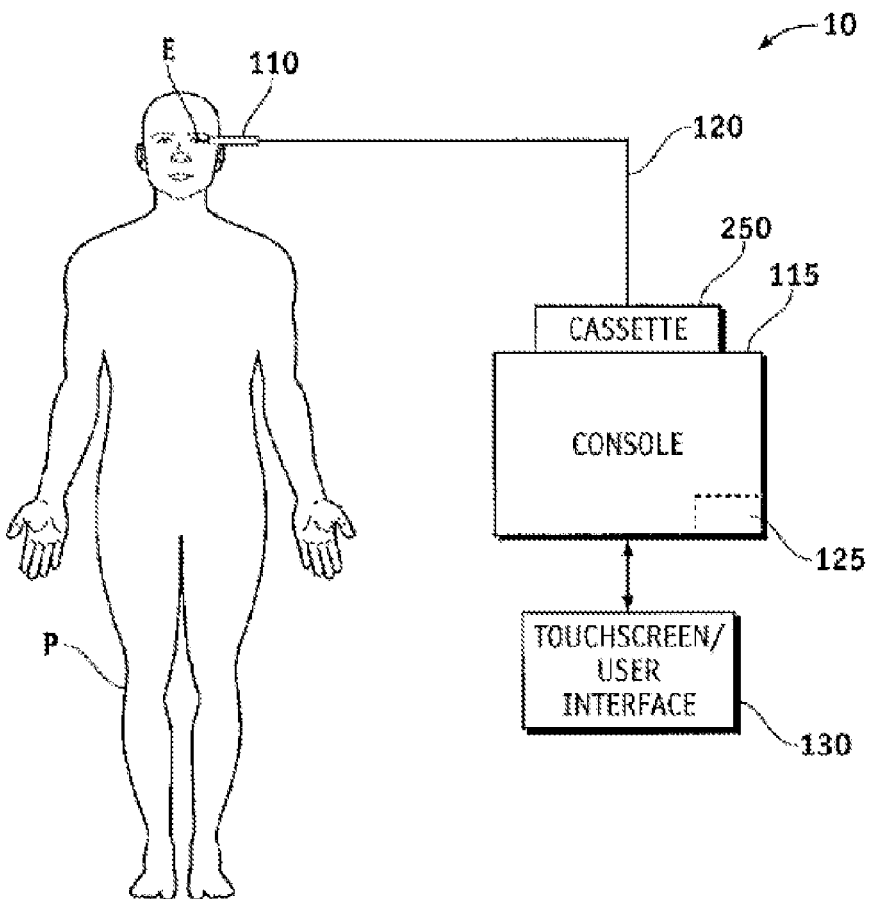
FIG. 1A is a schematic illustrating an eye treatment system in which a cassette is coupled to an eye treatment probe with an eye treatment console under one embodiment.

It is to be understood that the figures and descriptions of the present invention have been simplified to illustrate elements that are relevant for a clear understanding of the present invention, while eliminating, for the purpose of clarity, many other elements found in typical surgical, and particularly optical surgical, apparatuses, systems, and methods. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to the disclosed elements and methods known to those skilled in the art.

The figures and descriptions provided herein may have been simplified to illustrate aspects that are relevant for a clear understanding of the herein described apparatuses, systems, and methods, while eliminating, for the purpose of clarity, other aspects that may be found in typical similar devices, systems, and methods. Those of ordinary skill may thus recognize that other elements and/or operations may be desirable and/or necessary to implement the devices, systems, and methods described herein. But because such elements and operations are known in the art, and because they do not facilitate a better understanding of the present disclosure, for the sake of brevity a discussion of such elements and operations may not be provided herein. However, the present disclosure is deemed to nevertheless include all such elements, variations, and modifications to the described aspects that would be known to those of ordinary skill in the art.

Embodiments are provided throughout so that this disclosure is sufficiently thorough and fully conveys the scope of the disclosed embodiments to those who are skilled in the art. Numerous specific details are set forth, such as examples of specific components, devices, and methods, to provide a thorough understanding of embodiments of the present disclosure. Nevertheless, it will be apparent to those skilled in the art that certain specific disclosed details need not be employed, and that exemplary embodiments may be embodied in different forms. As such, the exemplary embodiments should not be construed to limit the scope of the disclosure. As referenced above, in some exemplary embodiments, well-known processes, well-known device structures, and well-known technologies may not be described in detail.

A surgical cassette, also referred to as a medical pack, a fluidic cassette, or simply, a cassette, is used to facilitate irrigation and aspiration during surgical procedures, such as phacoemulsification surgery. The surgical cassette may be inserted and mounted to a surgical console and become part of an overall phacoemulsification surgery system. The surgical cassette may perform a myriad of functions, such as effluent material collection, tube pressure sensing, and control the flow of fluid through tubing encased within the cassette and between a surgical handpiece and a surgical console.

A surgical cassette typically comprises a front plate and a back plate, and may also include a gasket at least partially there between. Other configurations of the cassette are contemplated with the present invention. Molded within either/or the front plate and the back plate may be pathways for fluid flow and/or for tubing to be inserted thereby creating desired pathways for the tubing around the gasket. In an embodiment where there is a gasket, the gasket may comprise one or more valves and one or more sensors to promote fluid flow through the tubing along the desired pathways. In another embodiment, a surgical cassette may have no tubing and/or gasket. In an embodiment where there is no gasket, any valves known in the art may be used, e.g., a rotary valve.

Surgical cassettes may utilize different types of sensors to monitor pressure, vacuum, and/or flow of certain fluid lines during the surgical process. Other single use cassettes may use a low-cost pressure diaphragm on the cassette with a console mounted Linear Variable Differential Transformer (LVDT) to measure the deflection of the pressure diaphragm with either a low rate spring pushing the LVDT against the surface of the pressure diaphragm or a magnet coupling the LVDT to the surface of the diaphragm, or a combination of both a spring and magnet. The spring force and/or friction force associated with movement of the LVDT sensing element reduces the accuracy and repeatability of this type system. Other systems may use laser triangulation displacement sensors to measure the deflection of a pressure diaphragm. In addition, other systems may use a ferromagnetic element in the cassette which couples to a magnetic element in the console, which may be coupled with a strain gauge.

Referring now to FIG. 1A, a system 10 for treating an eye E of a patient P generally includes an eye treatment probe handpiece 110 coupled with a console 115 by a cassette 250. Handpiece 110 generally includes a handle for manually manipulating and supporting an insertable probe tip. The probe tip has a distal end which is insertable into the eye, with one or more lumens in the probe tip allowing irrigation fluid to flow from console 115 and/or cassette 250 into the eye. Aspiration fluid may also be withdrawn through a lumen of the probe tip, with console 115 and cassette 250 generally including a vacuum aspiration source, a positive displacement aspiration pump, or both to help withdraw and control a flow of surgical fluids into and out of eye E. As the surgical fluids may include biological materials that should not be transferred between patients, cassette 250 will often comprise a sterilizable (or alternatively, disposable) structure, with the surgical fluids being transmitted through flexible conduits 120 of cassette 250 that avoid direct contact in between those fluids and the components of console 115.

When a distal end of the probe tip of handpiece 110 is inserted into an eye E, for example, for removal of a lens of a patient P with cataracts, an electrical conductor and/or pneumatic line (not shown) may supply energy from console 115 to an ultrasound transmitter of handpiece 110, a cutter mechanism, or the like. Alternatively, handpiece 110 may be configured as an irrigation/aspiration (I/A) and/or vitrectomy handpiece. Also, the ultrasonic transmitter may be replaced by other means for emulsifying a lens, such as a high energy laser beam. The ultrasound energy from handpiece 110 helps to fragment the tissue of the lens, which can then be drawn into a port of the tip by aspiration flow. So as to balance the volume of material removed by the aspiration flow, an irrigation flow through handpiece 110 (or a separate probe structure) may also be provided, with both the aspiration and irrigation flows being controlled by console 115.

To avoid cross-contamination between patients without incurring excessive expenditures for each procedure, cassette 250 and its flexible conduits 120 may be disposable. However, the flexible conduit or tubing may be disposable, with the cassette body and/or other structures of the cassette being sterilizable. Cassette 250 may be configured to interface with reusable components of console 115, including, but not limited to, peristaltic pump rollers, a Venturi or other vacuum source, a controller 125, and/or the like.

Console 115 may include controller 125, which may include an embedded microcontroller and/or many of the components common to a personal computer, such as a processor, data bus, a memory, input and/or output devices (including a user interface 130 (e.g. touch screen, graphical user interface (GUI), etc.), and the like. Controller 125 will often include both hardware and software, with the software typically comprising machine readable code or programming instructions for implementing one, some, or all of the methods described herein. The code may be embodied by a tangible media such as a memory, a magnetic recording media, an optical recording media, or the like. Controller 125 may have (or be coupled with) a recording media reader, or the code may be transmitted to controller 125 by a network connection such as an internet, an intranet, an ethernet, a wireless network, or the like. Along with programming code, controller 125 may include stored data for implementing the methods described herein, and may generate and/or store data that records parameters corresponding to the treatment of one or more patients.

Figure 1B:
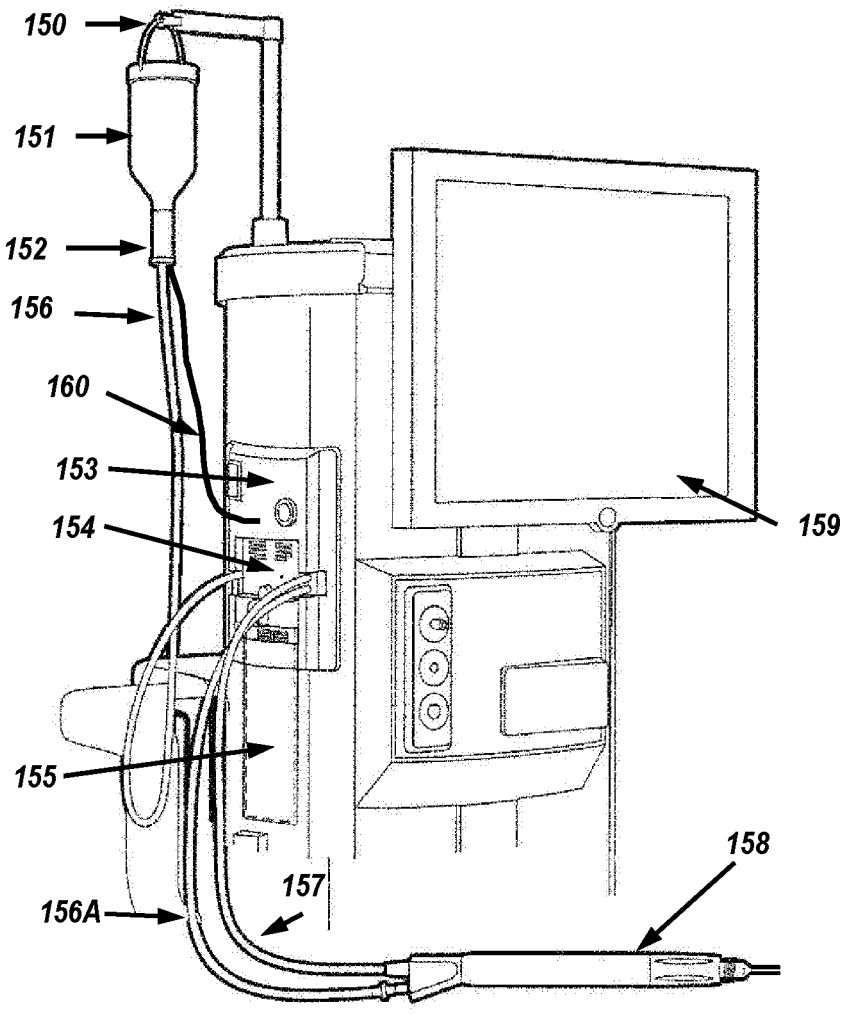
FIG. 1B is a schematic illustrating a surgical eye treatment console under another exemplary embodiment.

Referring now to FIG. 1B, a simplified surgical console is illustrated, where a fluid path may be demonstrated under an exemplary embodiment. In this example, an irrigation source 151 may be configured as a bottle or bag hanging from an IV pole hanger 150. It is understood by those skilled in the art that, while an integrated IV pole is illustrated, other configurations, utilizing standalone/static IV poles, pressurized infusion sources, and/or other suitable configurations, are contemplated by the present disclosure.

An exemplary irrigation path for fluid may be realized via tubing cassette 154 coupled with cassette tubing interface 153, which receives fluid from irrigation source 151 via drip chamber 152. Irrigation line 156A and aspiration line 157 are coupled to handpiece 158. Irrigation fluid may flow from drip chamber 152 through the irrigation tubing 156 into tubing cassette 154. Irrigation fluid may then flow from the tubing cassette through handpiece irrigation line 156A which may be coupled to an irrigation port on handpiece 158. Aspirated fluid may flow from the eye through the handpiece aspiration line 157 back to tubing cassette 154 and into a waste collection bag 155. A touch screen display 159 may be provided to display system operation conditions and parameters, and may include a user interface (e.g., touch screen, keyboard, track ball, mouse, etc.—see controller 125 of FIG. 1A) for entering data and/or instructions to the system of FIG. 1B.

Figure 2:
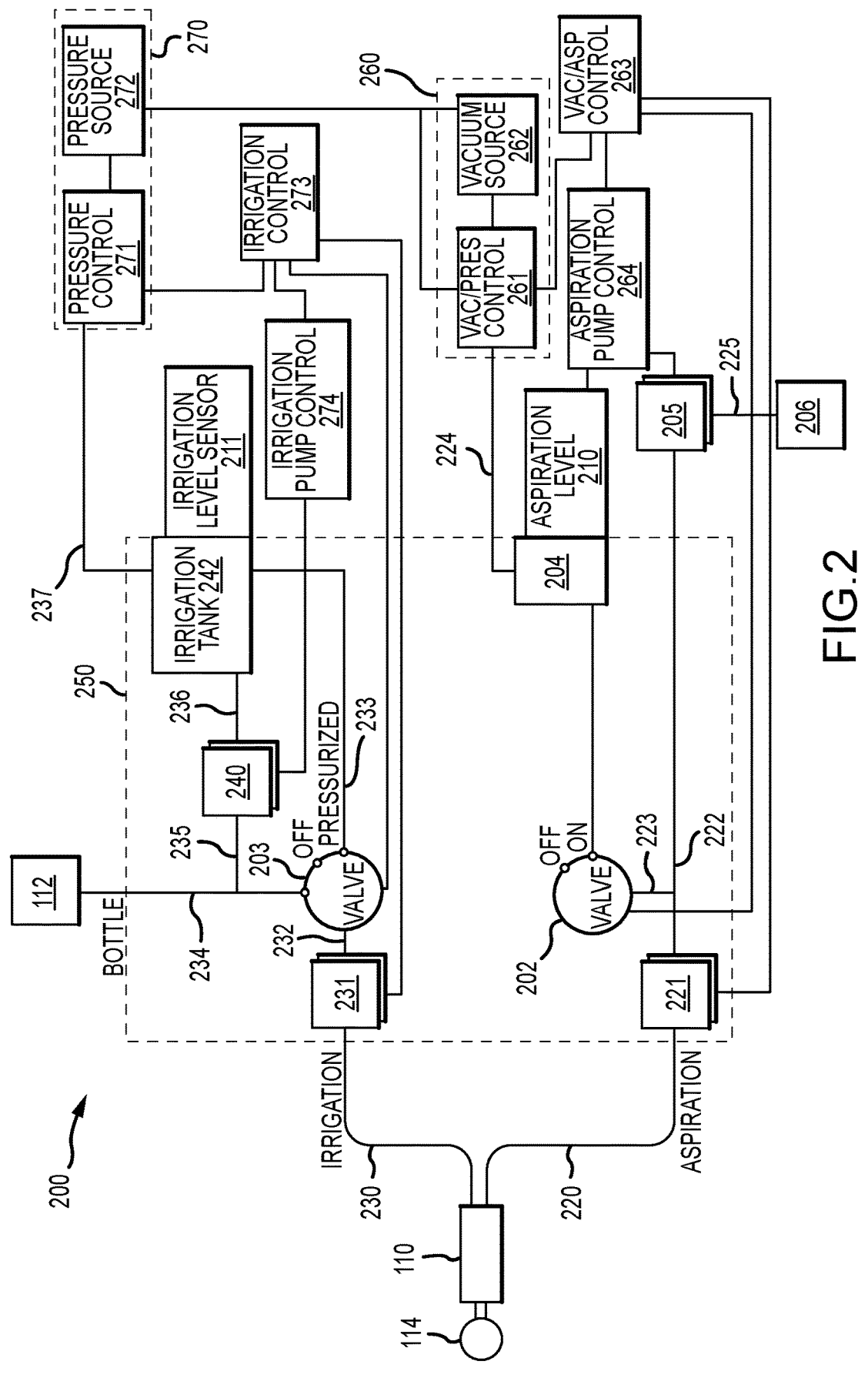
FIG. 2 is a functional block diagram of an exemplary cassette system for an eye treatment system under one embodiment.

Referring to FIG. 2, an exemplary cassette system showing some of the components and interfaces that may be employed in a phaco system, such as ones illustrated in FIGS. 1A-B. Handpiece 110 may be connected to (or coupled with) the input side of sensor 221, typically by fluid pathways such as fluid pathway 220. Sensor 221 may be a pressure, flow, or a vacuum sensor that measures pressure, flow or vacuum, respectively. In a preferred embodiment, sensor 221 is a pressure sensor. The output side of sensor 221 is connected to valve 202 and also connected to pump 205 within cassette 250 via fluid pathway 222. Valve 202 may be any known valve in the art, e.g., flow selector valve, rotary valve, etc. Valve 202 may also be coupled with pump 205. The exemplary embodiment may configure valve 202 to interface between handpiece 110, vacuum tank 204, pump 205, which may be a peristaltic pump but may be another type of pump, and collection 206. In this configuration, the system may operate valve 202 to connect handpiece 110 with vacuum tank 204 based on signals received from console 115 resulting from the surgeon's input to user interface 130. In an embodiment, the handpiece 110 is always connected to pump 205 and valve 202 and may be toggled to connect or disconnect the handpiece 110 to the tank 204. As discussed herein in greater detail, an aspiration level sensor 210 may be communicatively coupled to vacuum tank 204.

The valve 202 illustrated in FIG. 2 may provide a connection between vacuum tank 204 and fluid pathway 222. The exemplary embodiment is not limited to one valve and may be realized using two valves each having at least two output ports, possibly connected together to provide the functionality described herein. For example, a pair of two valves may be configured in a daisy chain arrangement, where the output port of a first valve is directly connected to the input port of a second valve. Console 115 may operate both valves together to provide three different flow configurations. For example, using two valves, valve one and valve two, valve one may use output port one, which is the supply for valve two. Valve two may connect to one of two ports providing two separate paths. When valve one connects its input port to its second output port rather than the output port that directs flow to the second valve, a third path is provided. It is also envisioned that valve 202 may be or comprise one or more pinch valves. The one or more pinch valves may be located along fluid pathway 220, 222 and/or 223, or any other fluid pathway as discussed herein.

Console 115 may also comprise vacuum pressure center 260 which may provide a vacuum through fluid pathway 224 to vacuum tank 204. The vacuum provided through fluid pathway 224 may be regulated by control module 261 based on signals received from aspiration control module 263 which may result from the surgeon's input to user interface 130 and/or based on other signals received from sensor 221. Aspiration control module 263 may also control pump control 264 and allow for operation of pump 205 for the movement of fluid from both the handpiece 110 and the vacuum tank 204 to collector 206 via pathway 225.

In the configuration shown, vacuum pressure center 260 includes a vacuum source 262, such as a venturi pump and an optional control module 261 (and valve (not shown)), but other configurations are possible. In this arrangement, vacuum pressure center 260 may operate to remove air from the top of vacuum tank 204 and deliver the air to atmosphere (not shown). Removal of air from vacuum tank 204 in this manner may reduce the pressure within the tank, which may reduce the pressure in the attached fluid pathway 220, to a level less than the pressure within eye 114. A lower reservoir pressure connected through valve 202 may cause fluid to move from the eye, thereby providing aspiration.

Thus, while a single valve 202 is illustrated in FIG. 2 associated with aspiration, it is to be understood that this illustration represents a valve arrangement, including one or more valves (e.g., flow selector valve, rotary valve, or the like) performing the functionality described herein, and is not limited to a single device or a single valve. In the exemplary sensor 221, a strain gauge or other suitable component may communicate or signal information to console 115 to provide an amount of vacuum sensed in the handpiece fluid pathway 220. Console 115 may determine the actual amount of vacuum present based on the communicated information.

Sensor 221 monitors the pressure of fluid flowing into and out of the line and can be used to determine when fluid flow should be reversed, such as encountering a certain pressure level (e.g., in the presence of an occlusion), and based on values obtained from the sensor 221, the system may control selector valve 202 and the pumps illustrated. It is to be understood that while components presented in FIG. 2 and other drawings of the present application are not shown connected to other system components, such as console 115, they are in fact connected for the purpose of monitoring and control of the components illustrated.

With respect to sensor 221, emergency conditions such as a dramatic drop or rise in pressure may result in a type of fail-safe operation. The exemplary embodiment employs sensor 221 to monitor the flow conditions and provide signals representing flow conditions to the system such as via console 115 for the purpose of controlling components shown including but not limited to selector valve 202 and the pumps shown. The fluid pathways or flow segments of surgical cassette system 200 may include the fluid connections, for example flexible tubing, between each component represented with solid lines in FIG. 2. In an embodiment, the fluid connections may include molded fluid channels.

Handpiece 110 may be connected to (or coupled with) the output side of irrigation sensor 231, typically by fluid pathways such as fluid pathway 230. Sensor 231 may be a pressure, flow, or a vacuum sensor that measures pressure, flow or vacuum, respectively. In a preferred embodiment, sensor 231 is a pressure sensor. The input side of irrigation sensor 231 may be connected to valve 203 within cassette 250 via fluid pathway 232. Valve 203 may be any known valve in the art, e.g., flow selector valve, rotary valve, etc. The exemplary embodiment may configure valve 203 to interface between handpiece 110, irrigation tank 242, pump 240, which may be a peristaltic pump but may be another type of pump, and irrigation fluid source 112. In this configuration, the system may operate valve 203 to connect handpiece 110 with gravity feed or pressurized irrigation based on signals received from console 115 resulting from the surgeon's input to user interface 130.

The valve 203 illustrated in FIG. 2 may provide a connection between irrigation tank 242, irrigation fluid source 112, and fluid pathway 232. The exemplary embodiment is not limited to one valve and may be realized using two valves each having at least two output ports, possibly connected together to provide the functionality described herein. For example, a pair of two valves may be configured in a daisy chain arrangement, where the output port of a first valve is directly connected to the input port of a second valve. Console 115 may operate both valves together to provide three different flow configurations. For example, using two valves, valve one and valve two, valve one may use output port one, which is the supply for valve two. Valve two may connect to one of two ports providing two separate paths. When valve one connects its input port to its second output port rather than the output port that directs flow to the second valve, a third path is provided. It is also envisioned that valve 203 may be or comprise one or more pinch valves. The one or more pinch valves may be located along fluid pathway 230, 232, 233, 234 and/or 235, or any other fluid pathway as discussed herein.

Console 115 may also comprise irrigation pressure center 270 which may provide a positive pressure through fluid pathway 237 to irrigation tank 242 using an applied pressure from pressure source 272 via pressure control 271. The pressure provided through fluid pathway 237 may be regulated by control module 271 based on signals received from irrigation control module 273 which may result from the surgeon's input to user interface 130 and/or based on other signals received from sensor 231. Irrigation control module 273 may also control pump control 274 and allow for operation of pump 240 for the movement of fluid from irrigation fluid source 112 to collector irrigation tank 242 via pathway 236. As discussed herein in greater detail, an irrigation level sensor 211 may be communicatively coupled to irrigation tank 242.

While a single valve 203 is illustrated in FIG. 2 associated with irrigation, it is to be understood that this illustration represents a valve arrangement, including one or more valves performing the functionality described herein, and is not limited to a single device or a single valve. In the exemplary irrigation sensor 231, a strain gauge or other suitable component may communicate or signal information to console 115 to provide an amount of pressure sensed in the handpiece fluid pathway 230. In another embodiment, depending upon the sensor used, an amount of vacuum or flow may be sensed in the handpiece fluid pathway 230 and communicated to console 115. Console 115 may determine the actual amount of pressure present based on the communicated information.

Figure 3:
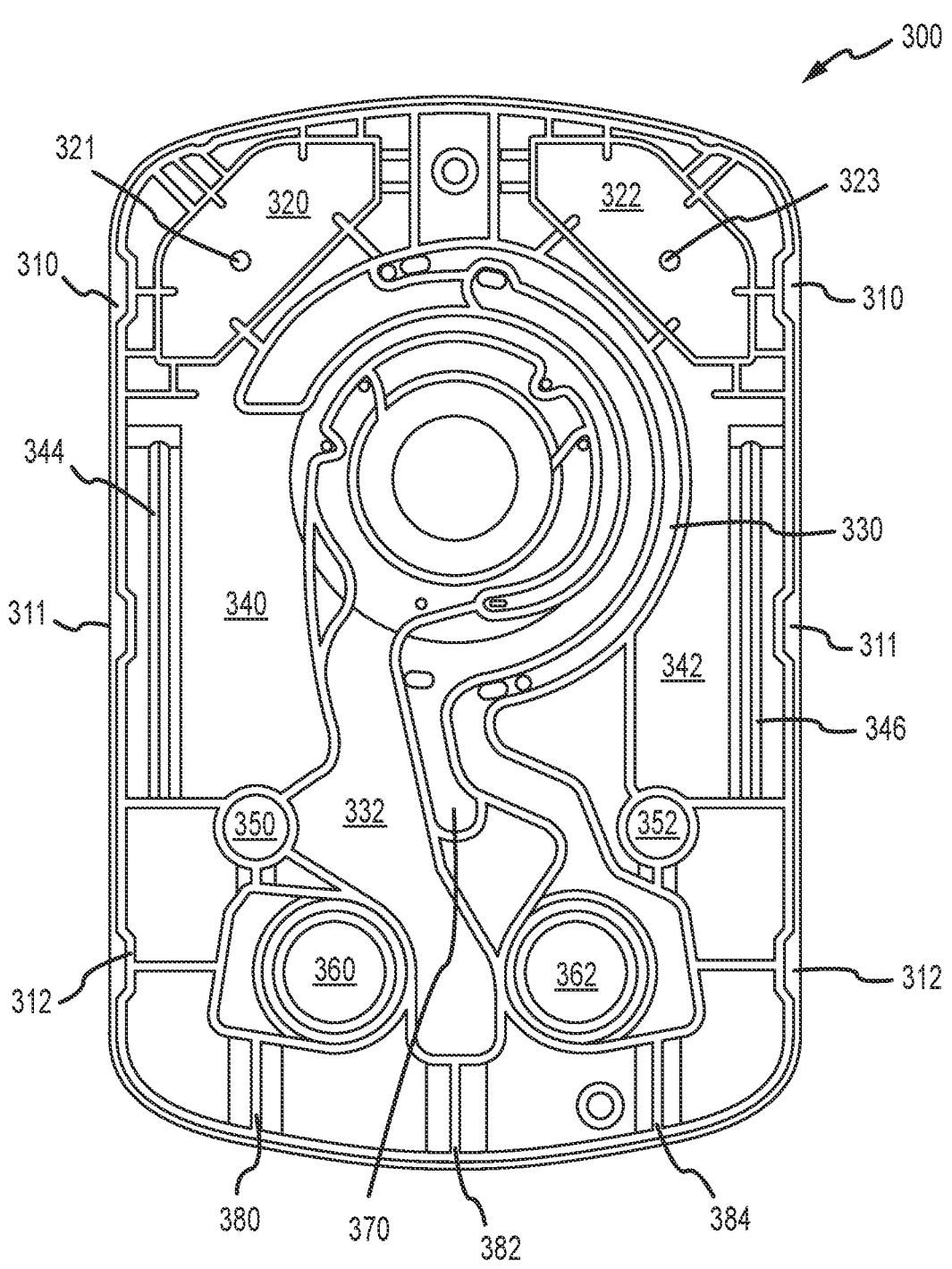
FIG. 3 is a schematic illustrating a cassette under another exemplary embodiment.

FIG. 3 illustrates an exemplary cassette system showing some of the features which may be employed in a phaco system. Cassette 300 may include a series of detents, also referred to as notches or catch surfaces, along its outer edge for receiving at least a portion of a retention device which may be associated with a surgical console to facilitate the retaining of the cassette to console and to at least partially assist in properly seating the cassette in the portion of the console meant to receive the cassette. As illustrated in FIG. 3, a cassette may include at least three sets of detents capable of accepting an attachment means provided by the console, such as, for example, upper detents 310, center detents 311, and lower detents 312. As will be described in greater detail below, the detents may be operated on in tandem or in a piecemeal fashion by a retention device of the surgical console.

An exemplary cassette may also include at least one pressurized fluid inlet 321 which may be in fluid communication with at least one filter within filter cavity 320. The pressurized fluid, for example, air, may be supplied to the cassette through fluid inlet 321 and introduced into pressurized irrigation tank 340 and may be in further communication with pressure sensor 360. There may similarly be at least one vacuum inlet 323 which may be in fluid communication with at least one filter within filter cavity 322. The vacuum applied through vacuum inlet 323 may be in communication with vacuum tank 342 and may be in further communication with aspiration channel 330 and aspiration channel 370. Each of the pressurized irrigation tank 340 and vacuum tank 342 may include a level sensing device 344 and 346, respectively.

Irrigation fluid may enter the cassette through inlet 382 and may enter irrigation channel 332. Irrigation valve 350 controls the flow path of irrigation fluid and may allow for gravity fed irrigation fluid to be supplied to irrigation outlet 380 from irrigation channel 332 or pressurized irrigation fluid from pressurized irrigation tank 340. In either instance, and even when irrigation valve 350 is in the "off" position relative to both irrigation fluid sources, the amount of pressure associated with the delivery of the irrigation fluid may be measured by irrigation sensor 360. Similarly, aspiration pressure may be measured by the aspiration sensor 362 in close proximity to aspiration inlet 384. Aspiration fluid which may enter though aspiration inlet 384 may enter aspiration channel 330 under pressure produced by at least one peristaltic pump, for example, and may also enter vacuum tank 342 under the influence of at least a partial vacuum through valve 352.

The console in conjunction with the cassette may provide fluid level sensing in each of the fluid tanks located within the cassette. Although many various mechanical techniques are well known to those skilled in the art, the present invention utilizes the difference in absorption between air and water-based fluids. More specifically, the present invention uses at least one sensor to detect the difference of reflectivity of the cassette-air versus cassette-water interface. Reflectivity is defined by the difference of refractive index (n) of materials where n (air)=1.00, n(water)=1.33, and n(cassette)=1.55. Using the following equation, $$r(n_1, n_2) = \left(\frac{n_1 - n_2}{n_1 + n_2}\right)^2$$

the reflectivity of the air and cassette interface is approximately 4.65%, while the reflectivity of the cassette and water interface is approximately 0.58%.

Figure 4:
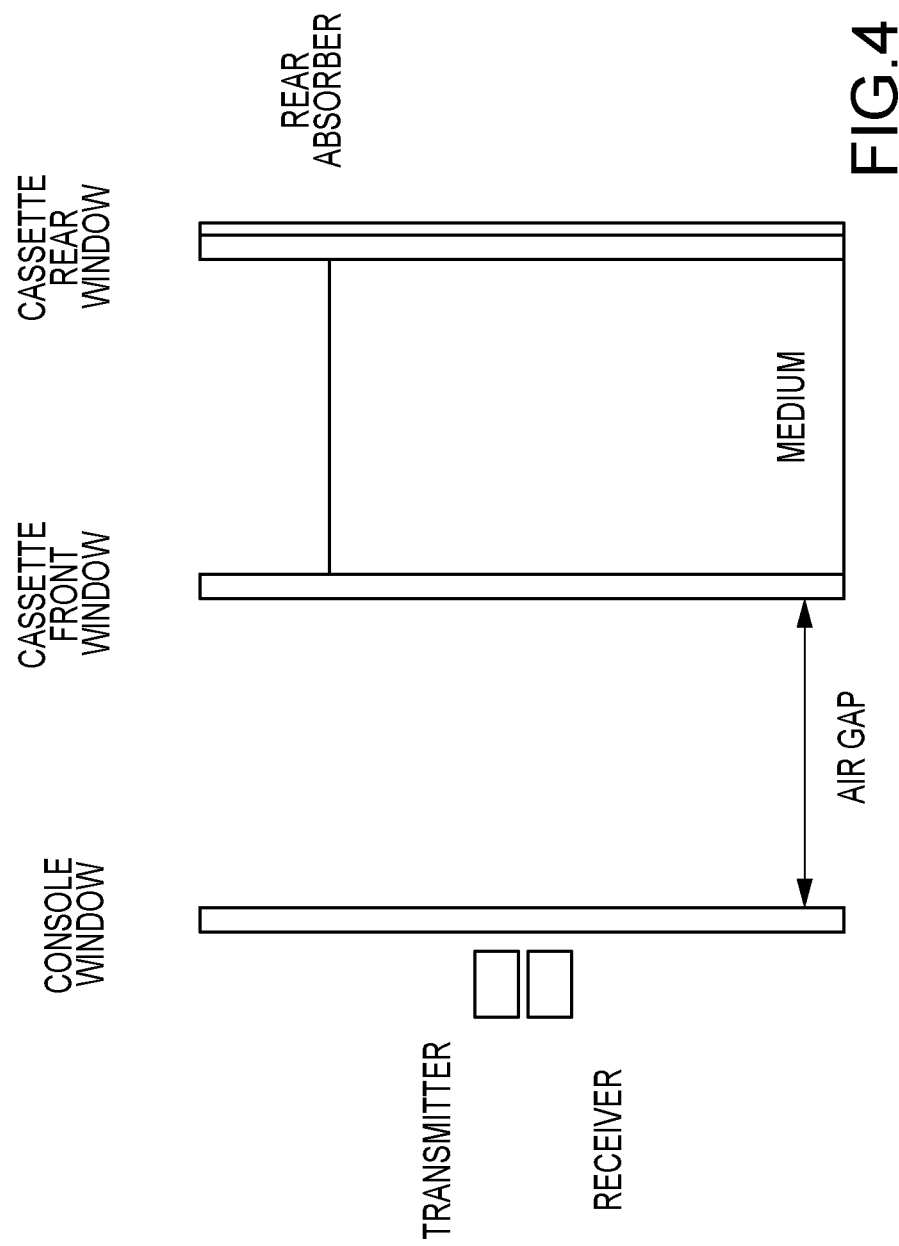
FIG. 4 is a diagram of an exemplary measurement method for use with a cassette system for an eye treatment system under one embodiment.

Although many types of sensors may be used to measure reflectivity, the use of infrared is preferred, such as through the use of a small IR reflectance sensor such a QRE1113, for example, which may have a maximum forward current of 50 mA and may operate at 940 nm. Such sensors include a transmitter and receiver node and are not susceptible to interference between each of the nodes. When IR is projected though the medium of air, more light is reflected back into the receiver than will be if the medium includes water. Similarly, the presence of air returns a lower voltage than when water is the pass-through medium. As illustrated in FIG. 4, an IR sensor having a transmitter and receiver may be located within a console behind a console window having a thickness of about 1 mm and being made of polycarbonate or like material. The gap between the console window and the front window of the cassette may be substantially zero and may be about 5 mm while the both the cassette windows may have a thickness up to about 1.5 mm. In an embodiment of the present invention, the cassette may employ a film or coating which may block and/or absorb ambient light to increase the measurable strength of the projected IR.

After a new cassette is inserted in to the receiving area of the console, the present invention may acquire level response for all sensors as a baseline measurement ($V_{empty}$). Once the system and the associated cassette is fully primed, the system may acquire level response for all sensor ($V_{full}$). In an embodiment of the present invention, when fully primed, at least one of the measured tanks of the cassette may be substantially full of fluid which condition may be determined based on an uppermost sensor voltage shift. Using the equation below results in a signal between 0 and 1.

$$V_{Sensor} = \frac{V - V_{empty}}{V_{full} - V_{empty}}$$

For example, $V_{sensor}>0.75$ may be indicative of the presence of water, while Water $V_{sensor}<0.75$ may indicate the presence of air.

Figure 5B:
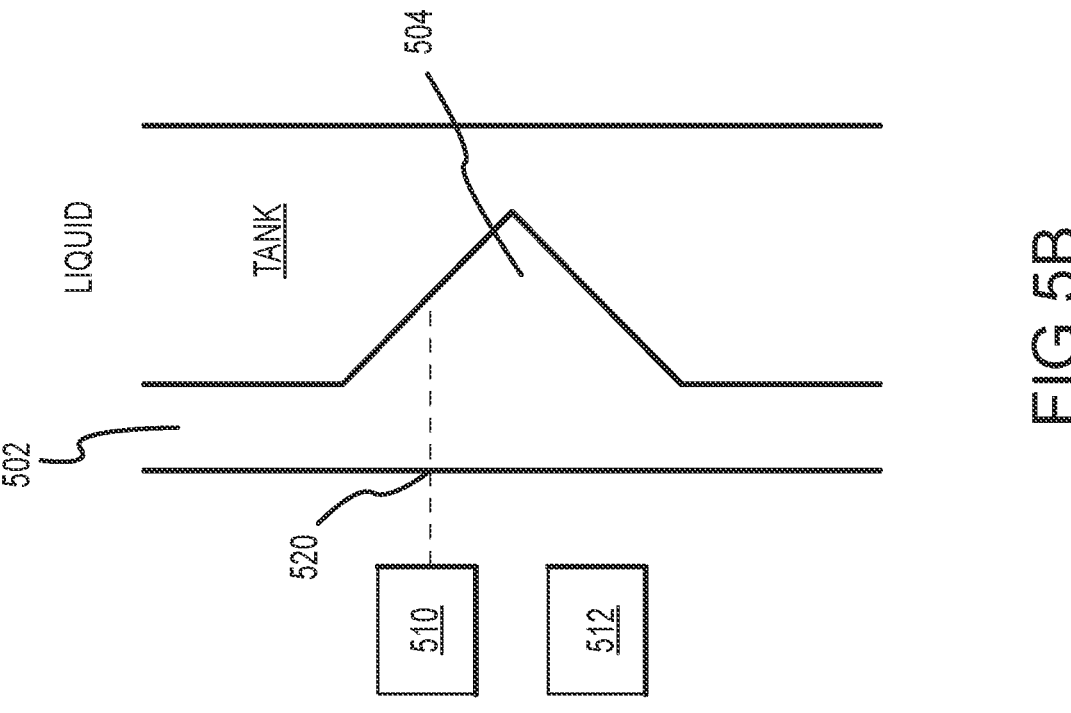
FIGS. 5A and 5B are partial schematics illustrating a level sensing device of a cassette under another exemplary embodiment.
Figure 5A:
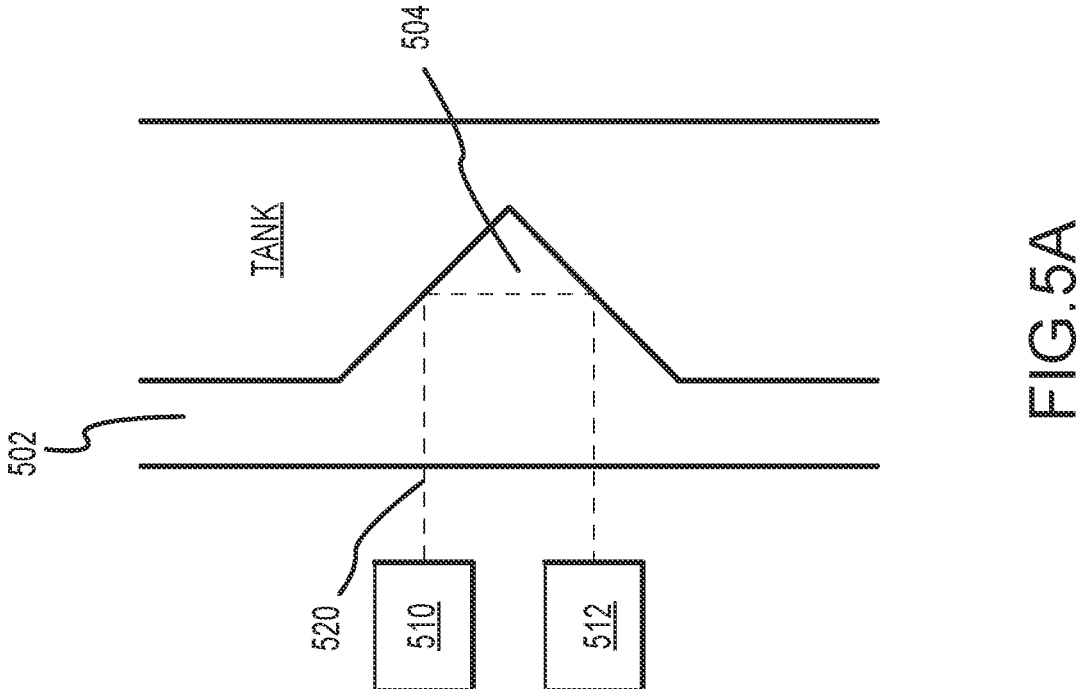

Each of the pressurized irrigation tank 340 and vacuum tank 342 may include a level sensing device 344 and 346, respectively. Each level sensing device may have a polygonal shape and may preferably have a triangular shape relative to the side wall of the tank which it is contained within. As illustrated in a top view cross section of a portion of a tank wall 502 having joined thereto a level sensing device 504 in FIG. 5A, transmission of an IR beam 520 from transmitter 510 may be substantially reflected back to the receiver 512 when the level sensing device is interfacing with air at the intersection of the IR beam 520 and the far edge of the level sensing device 504. As illustrated in FIG. 5B, when the same intersection of IR beam 520 and the far edge of the level sensing device 504 is at a liquid interface relative to the intersection, substantially the entire IR beam 520 passes into the liquid and not received by receiver 512.

Figure 6:
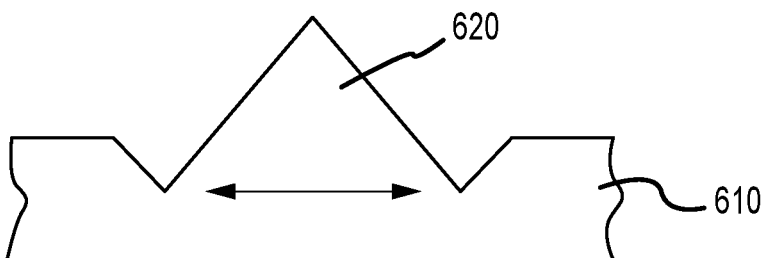
FIG. 6 is a partial schematic illustrating a level sensing device of a cassette under another exemplary embodiment.

As illustrated in FIG. 6, an exemplary embodiment may include a level sensing device 620 sunken into the wall of a tank 610. The width of the base of the level sensing device 620 may be between 2 mm and 5 mm; and may preferably be approximately 3.2 mm wide. The use of a polygonal shape such as a triangle versus no such level sensing device (e.g., just using a sensor through a flat tank wall) improves the reflectivity sensitivity of the sensor by more than 20 times. Thus, a triangular or other prism shape which may allow for the bending of light is preferable.

Each level sensing device may take additional shapes and may, for example, vertically extend over a majority of the height of the tank for which it resides. Over the length of the level sensing device, a plurality of sensors may be placed, with at least one sensor being near, or at the uppermost portion of the level sensing device for which a measurement is desired to be taken. Although just one sensor may be used to indicate a "full" tank status, for example, a series of sensors may allow for the incremental and accurate detection of fluid rise within a tank.

In an embodiment of the present invention, a level sensing device may not be used to detect the fluid level in a tank. Such a method of sensing reflection/absorption of light in the tank using the flat walls of a tank may be used alone or in conjunction with the use of a level sensing device. The sensing of fluid level through a flat wall may more accurately identify and signal the retention of liquid droplets, for example. The absence of a level sensing device may also allow for a less cumbersome tank design and/or easier manufacture of the tank. The accuracy of the sensors used in the present invention may also be assisted through the use of a reflector or absorber on a wall of the cassette. The reflecting or absorbing material may for a part of the tank wall, and/or may be a coating or other film-based application. For example, a material that may partially absorb the transmitted light may be placed on the exterior of the cassette wall on the opposite side of the cassette from the transceiver, which may augment the sensitivity of the sensor.

Figure 7A:
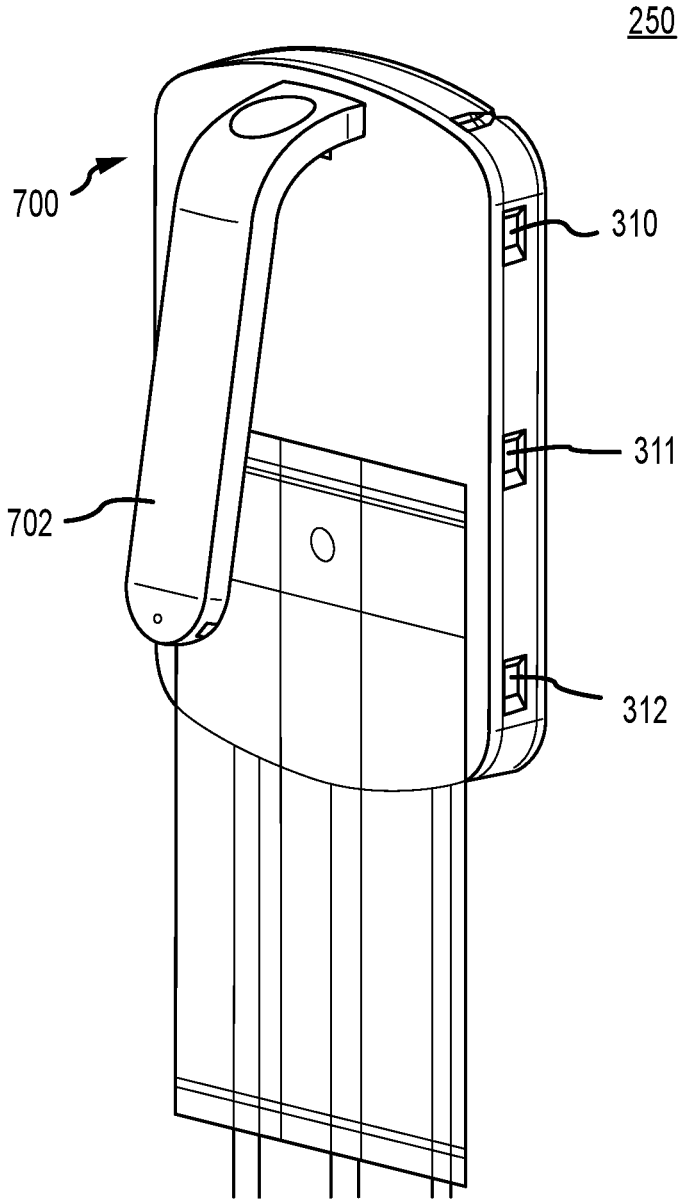
FIGS. 7A and 7B are illustrations of cassettes for use with an eye treatment system under one embodiment.
Figure 7B:
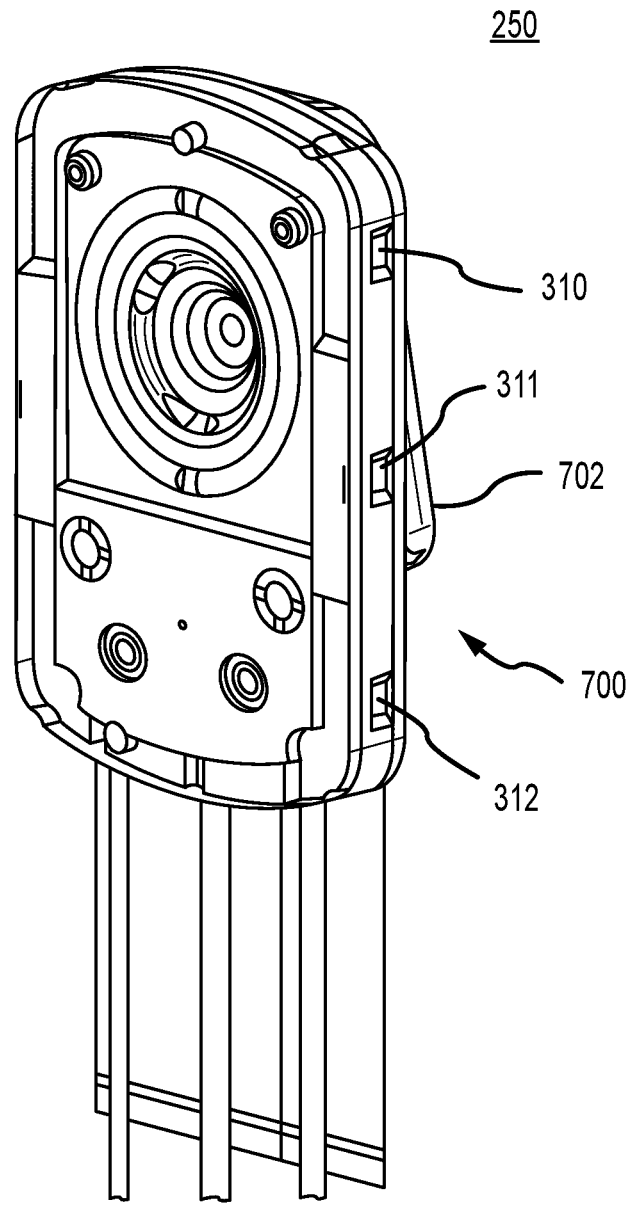

Engagement and alignment between cassette 250 and the interfacing structures of console 115 may be achieved through a variety of mechanisms, some of which are described in U.S. Pat. No. 8,491,528 to Muri et al., titled "Critical Alignment of Fluidics Cassettes" issued Jul. 23, 2013 and U.S. Pat. Pub. No. 2010/0249,693 to Jeremy T. Links, titled "Cassette Capture Mechanism," filed Mar. 31, 2009, each of which are incorporated by reference in their entirety herein. A cassette 250 may generally have a height and a width which generally are greater than a thickness of cassette 250 along a mounting axis, allowing the interfacing fluid pathway network elements of cassette 250 and corresponding components of a console to be distributed in a roughly planar configuration. In addition to the individual interfaces, as illustrated in FIGS. 7A and 7B, cassette 250 may generally include a cassette body 700 with at least three sets of detents capable of accepting an attachment means provided by the console, such as, for example, upper detent 310, center detent 311, and lower detent 312 and a handle portion 702. Cassette detents/notches partially define the positioning of the retention device that receives and positions cassette located within the console.

In one exemplary embodiment, cassette 250 is manually supported and advanced horizontally along a mounting axis until a corner of cassette 250 is detected by an alignment sensor associated with the console. One or more alignment sensors may be used; preferably two alignment sensors are employed with a cassette receptacle on the console. The alignment sensor may be an optical, magnetic, or any other detection mechanism known in the art. In one exemplary embodiment, cassette 250 is manually supported and advanced horizontally along a mounting axis until a portion of the cassette 250 is detected by a proximity detector associated with the console. One or more proximity sensors may be used; preferably at least one proximity sensor is employed with a cassette receptacle on the console and may be, for example, positioned to sense the relative distance of the body of the cassette 250 to the cassette receptacle. The proximity sensor may be an optical, magnetic, or any other detection mechanism known in the art.

In another embodiment, cassette 250 is manually supported and advanced horizontally along a mounting axis until a corner of cassette 250 is engaged by a capture plunger associated with the console. One or more capture plungers may be used; preferably at least two capture plungers are employed with a cassette receptacle on the console. The capture plunger may be a spring loaded actuator, or any other like mechanism known in the art, such as, for example, a hydraulic, pneumatic and/or electromechanical actuator which may or may not provide an electronic signal indicative of actuator movement. The capture plungers may, for example, prevent the cassette from falling out of preload position both before capture and after ejection.

In another console these plungers may comprise sensors to detect positioning features on another cassette thus eliminating the need for separate proximity sensors. In this case it was cheaper to make separate components.

Figure 8A:
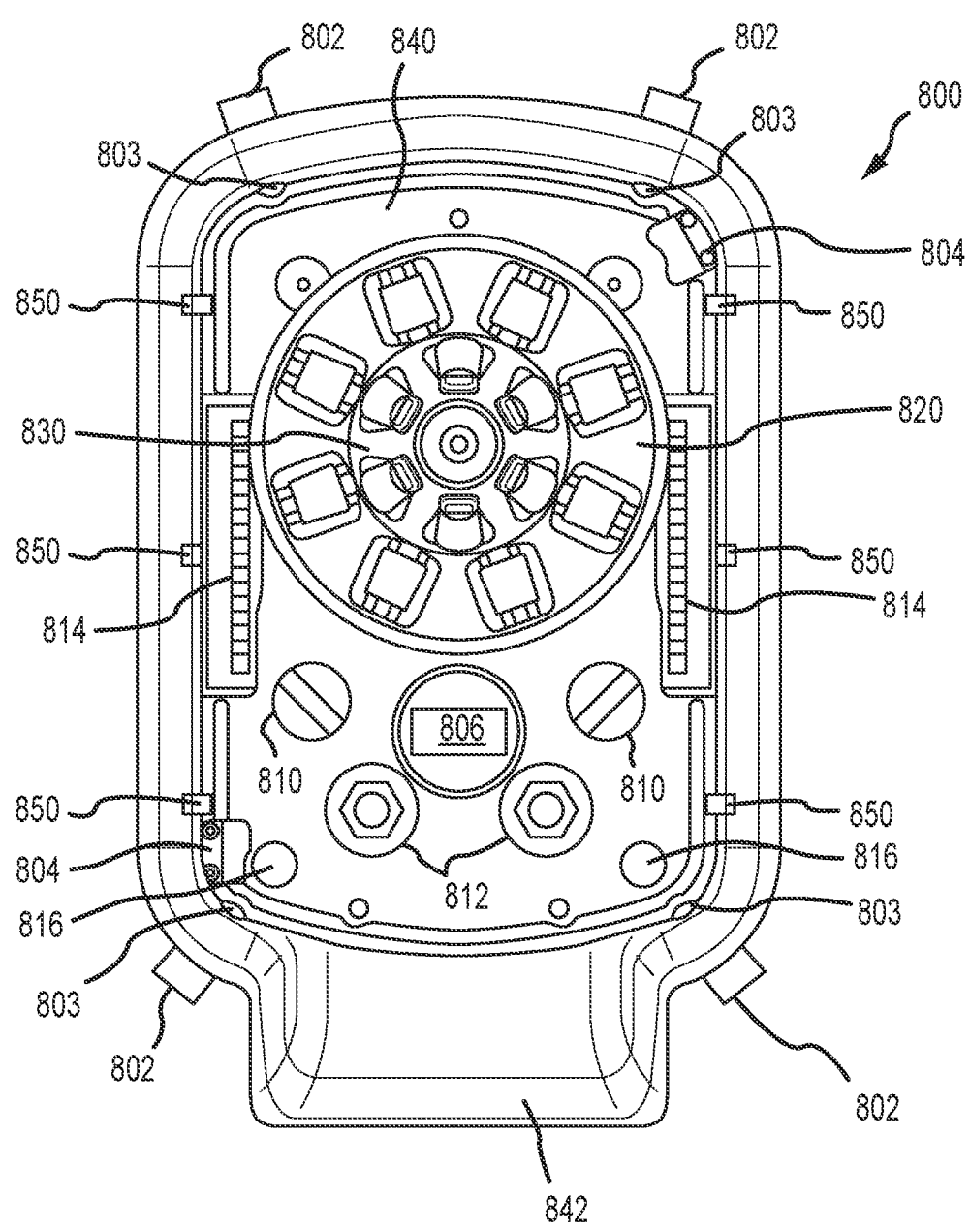
FIGS. 8A and 8B are illustrations of a cassette receiving area for use with an eye treatment system under one embodiment.

As illustrated in FIG. 8A, a cassette receptacle 800 which may be associated with a console is shown with various mechanical and electrical aspects that may interact with an inserted cassette. As would be appreciated by those skilled in the art, a cassette for use with the present invention may be sized to substantially occupy the at least the portion of the cassette receptacle 800 most proximate to the console and/or the distal wall 840 of the cassette receptacle 800. Similarly, the sidewall 842 of the cassette receptacle 800 may be shaped to at least partially surround and/or support a cassette. In an embodiment of the present invention, sidewall 842 may be partially open at the lower portion of the cassette receptacle 800 to accommodate tubing which may extend from the cassette.

In an embodiment of the present invention, the cassette receptacle may have a plurality of capture plungers 802 which may protrude through sidewall 842. As further illustrated in FIGS. 9A and 9B, a capture plunger may include an actuator and may have a body portion 802 and a tip portion 803. Each capture plunger may interface with an inserted cassette, and may provide physical stability and/or cassette alignment with the cassette receptacle. In an embodiment of the present invention, at least one capture plunger may be positioned in each corner area of the cassette receptacle such that at least a portion of the tip of the capture plunger can interface with the cassette.

Figures 9A, 9B:
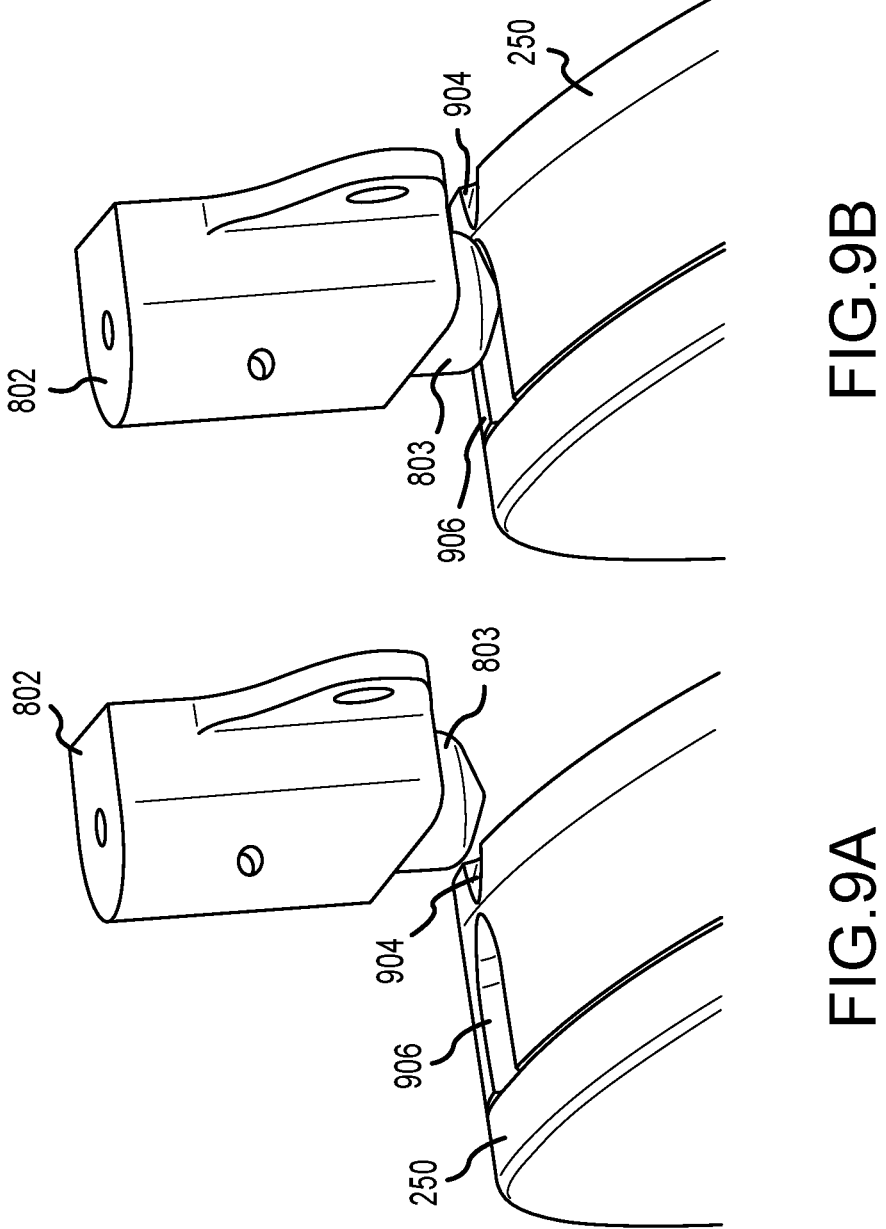
FIGS. 9A and 9B are illustrations of capture mechanisms for use with an eye treatment system under one embodiment.

More specifically, as illustrated in FIG. 9A, the cassette 250 may have a first receiving groove 904 and a second receiving groove 906. The first receiving groove 904 may be a detent open to the face of the cassette 205 and may perform as a ramp by which tip 803 of cassette plunger 802 may be actuated upwards allowing tip 803 to be guided to the second receiving groove 906. The second receiving groove 906 may have graduated or ramped sides and may be fully encompassed by the body of cassette 250. As illustrated in FIG. 9B, when the cassette 250 is positioned in cassette receptacle 800, the tip 803 of cassette plunger 802 may be below the outer surface of the cassette while at least partially within the second receiving groove 906. Thus, a cassette enters the cassette receptacle, the tip of each plunger may engage a first receiving groove and may rise to at least about the top of the entering cassette before descending into a second receiving groove which may secure that portion of the cassette in a position relative to the plunger.

Referring back to FIG. 8A, the cassette receptacle 800 may also include at least one alignment sensor 804. Each alignment sensor 804 may include at least one IR transmitter and receiver, and may, preferably, contain a pair of IR transmitters and receivers to obtain a two sensor array able of detecting a first position A and a second position B of a cassette relative to the cassette receptacle. In an embodiment of the present invention, at least two alignment sensors may be positioned at nearly opposite positions with the cassette receptacle such that upon a cassette entering the cassette receptacle, the cassette may be able to be detected by either first position A and/or a second position B or either alignment sensor. The alignment sensors may not be orientated such that they will detect a cassette at different angles and first position A may be proximate to the opening of the cassette receptacle.

By way of non-limiting example only, as a cassette is inserted into the cassette receptacle, the leading edge of the cassette will pass by and trigger each alignment sensor. Regardless of the positioning of each alignment sensor within the cassette receptacle, each of the first position A sensors are at the same depth relative to the rear wall of the cassette receptacle as well as each of the second position B sensors are at the same depth relative to the rear wall of the cassette receptacle. Using a cassette having sufficient rigidity and such cassette being constrained in size and shape to compliantly fit within the cassette receptacle will allow detection of the cassette by the by either first position A and/or a second position B to be translated into the real time orientation of the cassette.

The orientations which may be detected include empty, preloaded, loaded, and undefined. As illustrated in Table 1, below, using two alignment sensor arrays, each having a first position A and a second position B allows for:

TABLE 1

| PRESENCE SENSOR STATE TABLE | | | | |
|---|---|---|---|---|
| 1A | 1B | 2A | 2B | STATE |
| 0 | 0 | 0 | 0 | EMPTY |
| 0 | 0 | 0 | 1 | UNDEFINED |

TABLE 1-continued

| | | | | PRESENCE SENSOR STATE TABLE |
| 1A | 1B | 2A | 2B | STATE |
| --- | --- | --- | --- | --- |
| 0 | 0 | 1 | 0 | UNDEFINED |
| 0 | 0 | 1 | 1 | UNDEFINED |
| 0 | 1 | 0 | 0 | UNDEFINED |
| 0 | 1 | 0 | 1 | UNDEFINED |
| 0 | 1 | 1 | 0 | UNDEFINED |
| 0 | 1 | 1 | 1 | UNDEFINED |
| 1 | 0 | 0 | 0 | UNDEFINED |
| 1 | 0 | 0 | 1 | UNDEFINED |
| 1 | 0 | 1 | 0 | PRELOADED |
| 1 | 0 | 1 | 1 | UNDEFINED |
| 1 | 1 | 0 | 0 | UNDEFINED |
| 1 | 1 | 0 | 1 | UNDEFINED |
| 1 | 1 | 1 | 0 | UNDEFINED |
| 1 | 1 | 1 | 1 | LOADED |

A "preloaded" orientation, for example, may occur when the cassette has been manually placed in the console and may be fully engaged with each capture plunger being seated in a second receiving groove. However, in this orientation, the cassette has not been fully seated in the cassette receptable and has thus not been detected by the sensors of second position B. This "preloaded" orientation may also occur when the cassette is released from a fully seated position before removal of the cassette from the cassette receptacle. In addition to those listed above, other configurations of Table 1 may also be preferred. By way of non-limiting example only, the "preloaded" orientation may occur whenever sensor 1A and 2A are high by ignoring one or both of any signals relevant to sensors 1B and/or 2B. Choosing to ignore one or more of sensors 1B and 2B may result in a more robust initiation of pack capture, for example. Whether or not to ignore such signals may be reflective of a user controlled input, a time delay sequence, and/or other indicator indicative of the start of an attempt to load a cassette. Similarly, although only four sensors are illustrated in Table 1, any number of sensors may be used, for example, including the use of a plurality of sensors in an array. Additional sensors may, for example, provide for more accurate orientation sensing of the cassettes and provide for better redundancy.

A "loaded" orientation occurs when the cassette has been fully seated by the capture mechanism in the cassette receptacle and thus is detected by the sensors of first position A and second position B of each sensor array. Similarly, an "undefined" orientation is one that the cassette does not trigger any one of the other orientations, such as, for example, if a cassette is inserted unevenly, is not fully engaged by the capture plungers, is in transition between orientations, or when an object other than the cassette triggers an alignment sensor.

In an embodiment of the present invention, the alignment and position of a cassette may be detected and inferred by proximity sensors and the values generated as illustrated in Table 1. For example, the proximity sensors may have three distinct states: null, preloaded, loaded. The proximity sensors may take the form of small circuit boards each comprising two proximity sensors arranged adjacently and sequentially such that, for example, a first sensor changes state when the cassette is in preloaded position, then a second sensor changes state when cassette is in a loaded position. Each sensor may change states when the cassette blocks its "view".

Figure 8B:
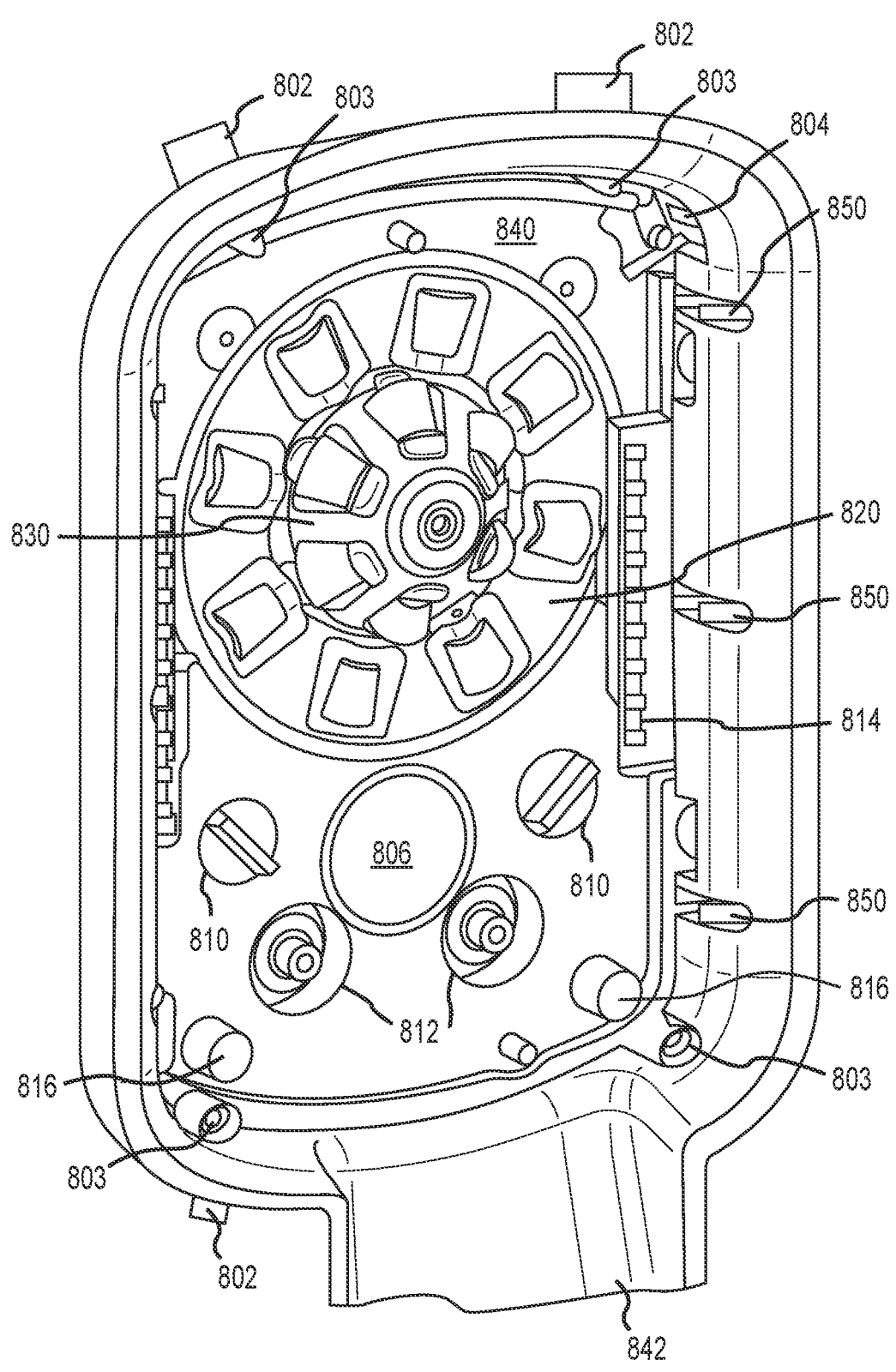

As further illustrated in FIG. 8B, the capture mechanism of the present invention may include a plurality of capture hooks 850 which may actuate behind the sidewall 842 of the cassette receptacle 800 and may engage cassette 250 in detents 310, 311, and 312. Upon engagement with the various sensors of the present invention as a cassette is being placed within the cassette receptacle 800, capture hooks 850 may engage detents 310, 311, and 312 and mechanically draw the cassette 250 into a fully seated position in the cassette receptacle 800. Capture hooks 850 may be semi-rigid to flexible to promote even force distribution along each vertical row of capture hooks. The fully seated position of the cassette would allow each aspect of the cassette receptacle to sufficiently operate on the cassette in their intended manner.

In an embodiment of the present invention, as the cassette is manually inserted into the console, it may first contact one or more of the capture plungers which may aid cassette alignment in the cassette receptacle. Under a relatively small insertion force (for example, 1.5 lb total when engaging four capture plungers) at least a portion of each of the capture plungers 802 may engage a corresponding detent on the cassette. Manual insertion into the console is then impeded by the cassette bladders contacting pump rollers and lower cassette face contacting collapsible pads 816. Each collapsible pad 816 is supported by a spring that is inside the pad housing. Each spring may have a nominal preload of about 1.7 lb and may be from about 0.5 to about 3 lbs. Thus, a 1.7 lb force is required to start moving the pad from the cassette preload position. In the capture position, when the cassette is fully seated in the cassette receptacle, the pad 816 spring load is about 2.4 lb each. The cassette detents and receptacle plungers may prevent the cassette from falling out of the console in at least the preloaded state.

A cumulative preset threshold insertion force is required to overcome springs that support pump head rollers and the collapsible pads and enable further insertion. Immediately after preload detection, capture hooks engage the cassette and pull it inward to the final support surfaces while causing the springs supporting pump rollers and collapsible pads to compress. Aspiration pump roller springs may require 35 lb. of total force to fully engage and may accept a force in the range of about 20 lbs. to about 50 lb. Irrigation pump roller springs may require 22 lbs. total of total force to fully engage and may accept a force in the range of about 10 lbs to about 40 lbs.

As illustrated in FIG. 8A, the present invention may also provide a proximity sensor 806 which may measure the real time distance of a cassette to the rear wall of the cassette receptacle. The proximity sensor 806 may use a low power IR emitter to illuminate an approaching cassette and measure the time it takes for a photon to return to the sensor. The proximity sensor 806 has a measurement range of between 1 cm to 30 cm and may perform measurements in 100 ms intervals with a resolution of 1 mm. Utilizing IR allows the sensor to measure distance independent of the reflectivity and color of the cassette and is capable of operating through the rear plastic wall of the cassette receptacle, or through a window made of glass or plastic, for example. As would be appreciated by those skilled in the art, the location of the proximity sensor may be varied and may be incorporated into other functional aspects of the cassette receptacle 800. For example, the proximity sensor could be situated between pressure sensors 812, for example. Furthermore, measurements taken by the proximity sensor 806 may be used by the console to activate various desired console functions.

As discussed above, an array of sensors may be used with and along each level sensing device. Such an array may extend along nearly the entire length of the level sensing device and may be positioned within the cassette to be centered on the vertical axis of the level sensing device. Each sensor array 814 may be set behind the rear wall of cassette receptacle 800 and may each contain between 2 and 16 sensors which may, for example, independently detect the presence of liquid within a tank associated with a level sensing device. Such an array of sensors may also support and/or include proximity sensors, for example. Similarly, such an array of sensors may be capable of supporting both proximity and fluid detection functions. As may be appreciated by those skilled in the art, a sensor array may also be a single sensor which may perform the same function as a group of one or more traditional IR sensors. The placement and orientation of a sensor array may be anywhere in which the measurement of fluid within an inserted cassette may be achieved.

The cassette receptacle may also include a pair of valve controls 810 which may interact and control valves within the cassette. The cassette receptacle may also include at least one pressure sensors 812 which may sense or otherwise read flow, vacuum, or pressure from certain portions of the cassette. Sensor 812 may be a pressure, flow, or vacuum sensor. In an embodiment, sensor 812 is a pressure sensor that may sense or otherwise read pressure from certain portions of the cassette. The cassette receptacle may also include aspiration pump head 820 and irrigation pump head 830 which may operate on a portion of the cassette 300.

Those of skill in the art will appreciate that the herein described apparatuses, engines, devices, systems and methods are susceptible to various modifications and alternative constructions. There is no intention to limit the scope of the invention to the specific constructions described herein. Rather, the herein described systems and methods are intended to cover all modifications, alternative constructions, and equivalents falling within the scope and spirit of the disclosure, any appended claims and any equivalents thereto.

In the foregoing detailed description, it may be that various features are grouped together in individual embodiments for the purpose of brevity in the disclosure. This method of disclosure is not to be interpreted as reflecting an intention that any subsequently claimed embodiments require more features than are expressly recited.

Further, the descriptions of the disclosure are provided to enable any person skilled in the art to make or use the disclosed embodiments. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein, but rather are to be accorded the widest scope consistent with the principles and novel features disclosed herein.

What is claimed is:

1. A system for phacoemulsification surgery, comprising:
a cassette receiving area for receiving a cassette having a sidewall shaped to at least partially surround an outer surface of the cassette, the cassette receiving area comprising at least two alignment sensors and a plurality of capture plungers, wherein each capture plunger is positioned within an opening in the sidewall and has a tip that protrudes through the sidewall, and wherein the tip is positioned below the outer surface of the cassette when the cassette is seated in the cassette receiving area; and
at least two capture hooks which are configured to engage with the cassette, wherein each of the at least two alignment sensors comprise two transceivers configured to collectively produce a first signal indicative of the cassette in a preloaded condition and a second signal indicative of the cassette in a loaded condition.

2. The system of claim 1, wherein the at least two alignment sensors comprises at least three alignment sensors.

3. The system of claim 1, wherein at least one of the plurality of capture plungers removably engages the cassette.

4. The system of claim 1, wherein at least one of the plurality of capture plungers is a spring loaded actuator.

5. The system of claim 1, wherein at least one of the plurality of capture plungers further provides a signal indicative of a height of the cassette.

6. The system of claim 1, wherein at least one of the plurality of capture plungers is proximate to a corner of the cassette receiving area.

7. The system of claim 1, further comprising at least one proximity sensor wherein the at least one proximity sensor measures a distance between the cassette and the cassette receiving area.

8. The system of claim 7, where in the at least one proximity sensor measures the distance at least every 100 milliseconds.

9. The system of claim 1, further comprising at least two collapsible pads suitable for engagement with the cassette.

10. A method for seating a surgical cassette in a phacoemulsification surgery console, the method comprising:
providing a cassette receiving area comprising at least two alignment sensors, the receiving area having a sidewall shaped to at least partially surround an outer surface of the surgical cassette;
providing a plurality of capture plungers, wherein each capture plunger is positioned within an opening in the sidewall and has a tip that protrudes through the sidewall, and wherein the tip is positioned below the outer surface of the surgical cassette when the surgical cassette is seated in the cassette receiving area; and
providing at least two capture hooks which are configured to engage with the surgical cassette, wherein each of the at least two alignment sensors comprise two transceivers configured to collectively produce a first signal indicative of the surgical cassette in a preloaded condition and a second signal indicative of the surgical cassette in a loaded condition.

11. The method of claim 10, wherein the at least two alignment sensors comprises at least three alignment sensors.

12. The method of claim 10, wherein at least one of the plurality of capture plungers removably engages the surgical cassette.

13. The method of claim 12, wherein at least one of the plurality of capture plungers is a spring loaded actuator.

14. The method of claim 10, wherein at least four signals are produced for each position of the surgical cassette.

15. The method of claim 10, further comprising at least one proximity sensor wherein the at least one proximity sensor measures a distance between the surgical cassette and the receiving area.

16. An apparatus for receiving a surgical cassette having an outer surface, comprising:
a cassette receiving area for receiving the surgical cassette, the cassette receiving area having a sidewall shaped to at least partially surround an outer surface of the surgical cassette, the cassette receiving area comprising at least two alignment sensors;

a plurality of capture plungers, wherein each capture plunger is positioned within an opening in the sidewall and has a tip that protrudes through the sidewall, and wherein the tip is positioned below the outer surface of the surgical cassette when the surgical cassette is seated in the cassette receiving area; and at least two capture hooks, wherein the at least two capture hooks are configured to securely engage in the surgical cassette, wherein each of the at least two alignment sensors comprise two transceivers configured to collectively produce a first signal indicative of the surgical cassette in a preloaded condition and a second signal indicative of the surgical cassette in a loaded condition.

17. The apparatus of claim 16, wherein the at least two alignment sensors comprises at least three alignment sensors.

18. The apparatus of claim 16, wherein at least one of the plurality of capture plungers removably engages the surgical cassette.

19. The apparatus of claim 16, wherein at least one of the plurality of capture plungers is a spring loaded actuator.

* * * * *